(12) United States Patent
Li et al.

(10) Patent No.: US 11,638,595 B2
(45) Date of Patent: May 2, 2023

(54) RECOVERY DEVICE OF GOLD MARKER FOR RADIOTHERAPY POSITIONING AND USING METHOD THEREOF

(71) Applicant: Fujian Medical University Union Hospital, Fujian (CN)

(72) Inventors: Xiaobo Li, Fujian (CN); Benhua Xu, Fujian (CN); Fen Zheng, Fujian (CN); Yuangui Chen, Fujian (CN); Fangfen Dong, Fujian (CN); Jing Chen, Fujian (CN); Lanyan Guo, Fujian (CN); Cheng Chen, Fujian (CN); Qizhen Xu, Fujian (CN); Jianping Zhang, Fujian (CN); Shanting He, Fujian (CN); Liuqing Jiang, Fujian (CN)

(73) Assignee: Fujian Medical University Union Hospital, Fujian (CN)

( * ) Notice: Subject to any disclaimer, the term of this patent is extended or adjusted under 35 U.S.C. 154(b) by 366 days.

(21) Appl. No.: 17/142,240

(22) Filed: Jan. 6, 2021

(65) Prior Publication Data
US 2022/0022995 A1 Jan. 27, 2022

(30) Foreign Application Priority Data

Jul. 21, 2020 (CN) .......................... 202021449451.0
Nov. 4, 2020 (CN) .......................... 202011217340.1
Nov. 4, 2020 (CN) .......................... 202022523564.7

(51) Int. Cl.
*A61B 17/34* (2006.01)
*A61B 90/00* (2016.01)
(Continued)

(52) U.S. Cl.
CPC .... *A61B 17/3468* (2013.01); *A61B 17/22031* (2013.01); *A61B 17/24* (2013.01);
(Continued)

(58) Field of Classification Search
CPC .............. A61B 37/22031; A61B 37/24; A61B 37/3468; A61B 34/10; A61B 34/20;
(Continued)

(56) References Cited

U.S. PATENT DOCUMENTS

2006/0094923 A1* 5/2006 Mate .................... A61N 5/1014
600/7
2006/0182326 A1* 8/2006 Schildkraut .......... A61N 5/1049
378/65

OTHER PUBLICATIONS

Liqun Gong, et al., "CT-guided preoperative hookwire localization of lung nodule in video-assisted thoracic surgery", Chin J Clin Oncol vol. 42. No. 6, Jan. 15, 2015., pp. 357-359.
(Continued)

*Primary Examiner* — Jocelin C Tanner
(74) *Attorney, Agent, or Firm* — JCIP Global Inc.

(57) ABSTRACT

A gold marker recovery device for radiotherapy positioning and its using method comprises a positioning gold marker and a recovery clamp, the positioning gold marker comprises a gold marker body and an elastic fixed structure, the elastic fixed structure comprises a fixed segment, an extending segment and a spiral segment connected in sequence; the fixed segment is embedded in the gold marker body so that the fixed segment is closely connected with the gold marker body, A magnetic ball is arranged at one end of the gold marker body away from the extending segment; the recovery clamp comprises an operating handle, the rear end of the operating handle is connected with an outer sheath tube in a hollow structure, and the outer sheath tube is connected with a zipper for driving the clamp to open and close.

18 Claims, 4 Drawing Sheets

(51) Int. Cl.
*A61B 17/24* (2006.01)
*A61B 17/22* (2006.01)
*A61B 17/00* (2006.01)

(52) U.S. Cl.
CPC .... *A61B 90/39* (2016.02); *A61B 2017/00867* (2013.01); *A61B 2017/00876* (2013.01); *A61B 2017/22035* (2013.01); *A61B 2017/242* (2013.01); *A61B 2090/3966* (2016.02); *A61B 2090/3983* (2016.02); *A61B 2090/3987* (2016.02)

(58) Field of Classification Search
CPC .......... A61B 90/39; A61B 2017/00867; A61B 2017/00876; A61B 2017/242; A61B 2034/107; A61B 2034/108; A61B 2034/2051; A61B 2034/2065; A61B 2090/3908; A61B 2090/3966; A61B 2090/3983; A61B 2090/3987; A61B 2090/3991; A61N 5/1049; A61N 2005/1096; G16H 20/40
See application file for complete search history.

(56) References Cited

OTHER PUBLICATIONS

Li Dong, et al., "The Clinical Applicability of CT-guided Hook-wire Puncture Positioning in the Diagnosis and Treatment of Pulmonary Nodules before Thoracoscopic Surgery", Zhe Jiang Medical, vol. 39, Issue 13, Sep. 15, 2017, pp. 1-5.

\* cited by examiner

RECOVERY DEVICE OF GOLD MARKER FOR RADIOTHERAPY POSITIONING AND USING METHOD THEREOF

CROSS-REFERENCE TO RELATED APPLICATION

This application claims the priority benefits of China application serial no. 202021449451.0, filed on Jul. 21, 2020, China application serial no. 202011217340.1, filed on Nov. 4, 2020 and China application serial no. 202022523564.7, filed on Nov. 4, 2020. The entirety of each of the above-mentioned patent applications is hereby incorporated by reference herein and made a part of this specification.

BACKGROUND OF THE DISCLOSURE

1. Field of the Disclosure

The present disclosure relates to the technical field of medical devices, in particular to a recovery device of gold marker for radiotherapy positioning and its using method.

2. Description of Related Art

Along with the development of radiotherapy technology, the development of precision radiotherapy technology improves the curative effect of radiotherapy and reduces side effects. Before cyber knife treatment, image guide is often required for implanting the gold marker near the tumor (that is, target area), so as to track the location of the tumor during the cyber knife treatment, thus achieving accurate treatment. The gold marker usually adopts pure gold particles with a length of 3-5 mm and a diameter of 0.70-0.80 mm. The real-time location of tumor is acquired by digital image, and the therapeutic rays are guided for automatic correction. The existing gold marker is designed on the shape of a cylinder, when implanted in the human body the gold marker of such form is easy to lose or displace due to the patient's breathing and cough, it is prone to cause great position deviation in the entire treatment process, resulting in deviation of the cancer treatment and thus affecting the treatment effect, such phenomenon is particularly obvious when the tumor is located in the lung, and the trachea and bronchial structure of the lung makes it difficult to realize the positioning effect of the gold marker of conventional structure, and displacement of the gold marker is quite common. Further, since the gold marker used in the existing radiotherapy has not been taken out after the treatment, and due to the frequent movement of the lung caused by breathing, the gold marker moves continually, which will cause certain impact on the human body.

Radiotherapy is one of the important treatment methods for lung malignancies, especially for those inoperable lung cancer patients, radiotherapy can alleviate symptoms, prolong patients' survival time and improve their quality of life. With the development of radiotherapy technology with image guidance and respiratory gating, cyber knife (stereotactic radiotherapy) has becoming more and more important in the treatment of early stage lung cancer. The principle of radiotherapy is to provide an accurate and even therapeutic dose matched with the tumor volume, increase the therapeutic dose of the treatment area as much as possible, and reduce the therapeutic dose received by the normal tissue around the irradiation area so as to protect the important organs around the tumor as much as possible. In order to make sure that the beam of radiotherapy accurately acts on the target area, precise positioning of the pulmonary nodule or lung tumor before the radiotherapy and real-time tracing of the lesions during the radiotherapy become quite important.

At present, the gold marker tracking and positioning technique before lung cancer radiotherapy is mainly in the form of CT-guided percutaneous gold marker implantation, CT-guided percutaneous Hook-wire positioning is the most commonly used preoperative positioning method for the positioning of pulmonary nodules, the success rate of puncture is 58%-100% (*CT-guided Preoperative Hook-wire Localization of Lung Nodule in Video-assisted Thoracic Surgery*, Chinese Journal of Clinical Oncology, 2015); when the patient is pathologically confirmed to suffer from a malignant tumor, under the guidance of CT, 4-5 metal markers (gold marker) with high atomic number have to be implanted in different places around the area of lung lesions through puncture, so as to form a visual target for tumor radiotherapy, and CT simulated positioning scan can be performed when the positions of the gold markers become stable after 5-7 days. Since percutaneous puncture is prone to cause complications such as pneumothorax, hemorrhage and leakage of pleural effusion, it is necessary to observe the patient's condition closely.

For the gold marker implanted by CT-guided percutaneous puncture, displacement of the gold marker occurs easily, or the gold marker will be discharged from the body through bronchial tube, 22.4% of patients have suffered from hemo-pneumothorax (*Clinical application of CT-guided Preoperative Hook-wire Positioning of Lung Nodule in Video-assisted Thoracic Surgery* Zhejiang Medical Journal, 2017). In addition, the gold marker is prone to displace due to breathing, posture change and so on, and the chance of positioning failure caused by the displacement of the gold marker is 4%-20%, and the gold marker implanted by puncture can not be taken out for recycling and has to remain in the patient's body for a long time after the radiotherapy treatment. At present, the gold marker has not obtained the registration certificate (Category III) of CFDA, thus can not be used in clinical practice and is the bottleneck of the development of the gold marker tracking technology of the cyber knife.

SUMMARY OF THE DISCLOSURE

The disclosure aims at overcoming the shortcomings of the prior art and provides a recovery device of gold marker for radiotherapy positioning with good positioning effect, no damage and recyclable, and a using method thereof.

The present disclosure is realized by the following means:

A recovery device of gold marker for radiotherapy positioning comprises a positioning gold marker and a recovery clamp, the positioning gold marker comprises a gold marker body and an elastic fixed structure, the elastic fixed structure comprises a fixed segment, an extending segment and a spiral segment connected in a sequential manner, the fixed segment is embedded in the gold marker body, so that the connection between the fixed segment and the gold marker body is tight and relative sliding or displacement between the fixed segment and the gold marker body is avoided, an end of the gold marker body away from the extension segment is provided with a magnetic ball, the recovery clamp comprises an operating handle, a rear part of the operating handle is connected with an outer sheath tube (2) in a hollow structure, a zipper (3) for driving a clamp (4) to open and close is movably linked in the outer sheath tube.

Further, the fixed segment is embedded in the magnetic ball, so that tight connection between the fixed segment and the magnetic ball is guaranteed and relative sliding or displacement between the fixed segment and the magnetic ball can be prevented.

Further, the gold marker body is made of a material that does not project an X-ray.

Further, the elastic fixed structure is made of superelastic material.

Further, when a force is applied to a terminal end of the spiral segment of the elastic fixed structure, the elastic fixed structure becomes straightened or compressed, and when the force disappears, the elastic fixed structure restores to its original shape.

Further, the clamp comprises a support cylinder, a distal end of the support cylinder is connected with a clamp head, the zipper penetrates a proximal end of the support cylinder and is connected with the clamp head, and the clamp head can open and close by pushing and pulling the zipper.

Further, the clamp head comprises a first half claw and a second half claw; the first half claw is hinged to the support cylinder and the zipper respectively, the second half claw is fixed to the support cylinder.

Further, the first half claw is respectively hinged to the supporting cylinder and the zipper through a connecting part, and the connecting part is provided with a permanent magnet.

Further, the first half claw and the second half claw are hemispherical.

A using method of the recovery device of gold marker for radiotherapy positioning comprises the following steps:

S1: Construct a 3D model of the patient's lung according to the three-dimensional reconstruction of two-dimensional CT images to determine the focus area.

S2: Determine several implantation points of the positioning gold marker around the three-dimensional space outside the focus area, the number of the implantation points is 3-6, and the minimum distance between two implantation points shall not be less than 20 mm, a minimum angle of a triangle formed by any three implantation points in the three-dimensional space shall be larger than 15°, a distance from the implantation points to the focus area shall not be greater than 20-30 mm, all the implantation points are visible in a 45° oblique view without overlap;

S3: Plan an implantation path through the 3D model of the patient's lungs according to the several implantation points established.

S4: An electromagnetic navigation bronchoscope reaches the implantation point according to the implantation path established, a medical channel is formed by the electromagnetic navigation bronchoscope after reaching the implantation point, and the positioning gold marker is implanted into the implantation point along the medical channel by a pushing device, and when the positioning gold marker is being implanted, the gold marker body is positioned behind the spiral segment, and the rest positioning gold markers are implanted into the corresponding implantation points successively in the above way.

S5: After the treatment, plan a removing path of the positioning gold marker according to the latest location information of the positioning gold marker acquired by CT and the 3D model of the patient's lung.

S6: The electromagnetic navigation bronchoscope reaches the target area according to the removing path established, a medical channel is formed by the electromagnetic navigation bronchoscope after reaching the target area, the clamp head of the recovery clamp penetrates through the medical channel in open state and reaches the target area where the positioning gold marker is located, and then the positioning gold marker is retrieved through the magnetic attraction force of the permanent magnet and the action of the clamp head, and the rest gold markers are removed from the body successively in the above manner.

The beneficial effect of the disclosure is that the gold marker can be effectively fixed in the lung trachea by the spiral segment of the gold marker structure, thus effectively preventing the gold marker displacement caused by respiration and improving the accuracy of radiotherapy. Through the electromagnetic navigation bronchoscope and 3D model of patient's lung, the implantation path can be quickly established and rapid and precise implantation of the gold marker is realized. The gold marker can be easily retrieved through the cooperation of the clamp in the recovering clamp and the magnetic ball. The whole procedure is non-invasive, patient's pain has been reduced, and the potential risks for living the gold markers in the trachea have also been reduced.

BRIEF DESCRIPTION OF THE DRAWINGS

In order to give a clearer description of the technical scheme of the embodiments of the disclosure, a brief description of the accompanying drawings to be used in the embodiments is given below. It should be understood that the accompanying drawings show only some embodiments of the present disclosure, and therefore should not be regarded as limiting the scope. For those skilled in the art, other relevant accompanying drawings can be obtained on the basis of these accompanying drawings without the cost of creative labor.

DESCRIPTION OF THE EMBODIMENTS

In order to explain the purpose, technical scheme and advantages of the embodiments of the disclosure more clear, the technical scheme of the embodiments of the disclosure will be clearly and completely described according to the accompanying drawings, and it is obvious that the embodiments of the disclosure are a part of the embodiments of the disclosure. Based on the embodiments of the disclosure, all other embodiments obtained by the ordinary technical personnel in this field without creative labor are within the scope of protection of the disclosure. Therefore, the descriptions of the above specification and embodiments are intended to explain the protection scope of the present disclosure, but do not constitute a limitation to the protection scope of the present disclosure. Based on the embodiments of the disclosure, all other embodiments obtained by the ordinary technical personnel in this field without creative labor are within the scope of protection of the disclosure.

In the description of the disclosure, the terms "up", "down", "in", "outside", "front end", "rear end", "both ends", "one end", "the other end" and the like are the orientations and position relationships shown based on the drawings, and the orientations and position relationships are for ease of description only and do not imply that the apparatus or element referred to must have a specific orientation or be constructed and operated in a specific orientation; therefore, these terms cannot be interpreted as a limitation to the specific protection scope of the present disclosure. Moreover, the terms "first" and "second" are used only for descriptive purposes and cannot be interpreted as indicating or implying relative importance.

In the description of the disclosure, it is necessary to state that, unless otherwise expressly specified and defined, the terms "installation", "comprising", "connection", etc. shall be understood in a broad sense, such as "connection" could be fixed connection, a detachable connection, or an integrated connection; either a mechanical connection, or an electrical connection; a direct connection, or an indirect connection through an intermediate medium, or an internal connection between two elements. For those skilled in the art, the specific meaning of the term in the disclosure should be interpreted according to specific situation.

Embodiment I

Figure 1:
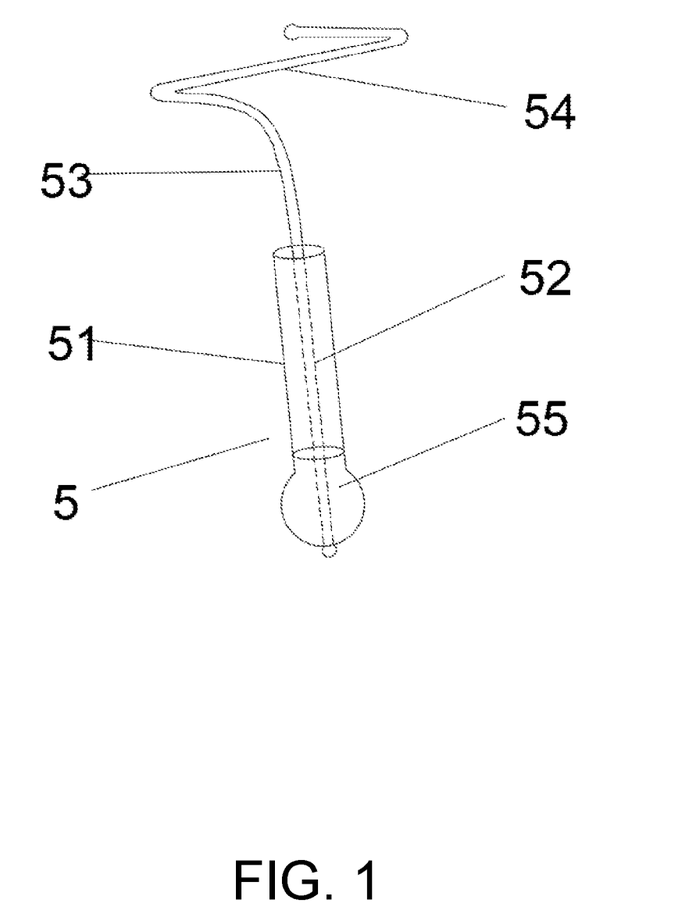
FIG. 1 is a structural schematic of a positioning gold marker of the embodiments of the disclosure.
Figure 2:
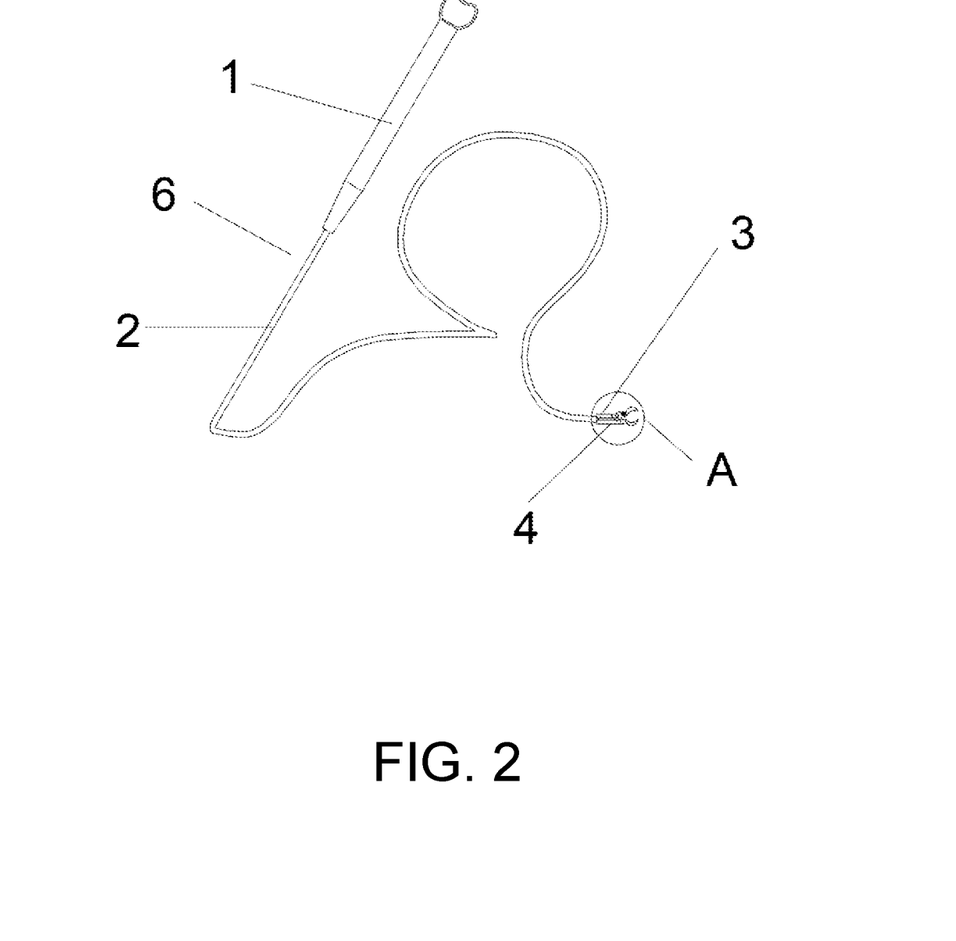
FIG. 2 is a structural schematic of a recovery clamp of the embodiments of the disclosure.
Figure 3:
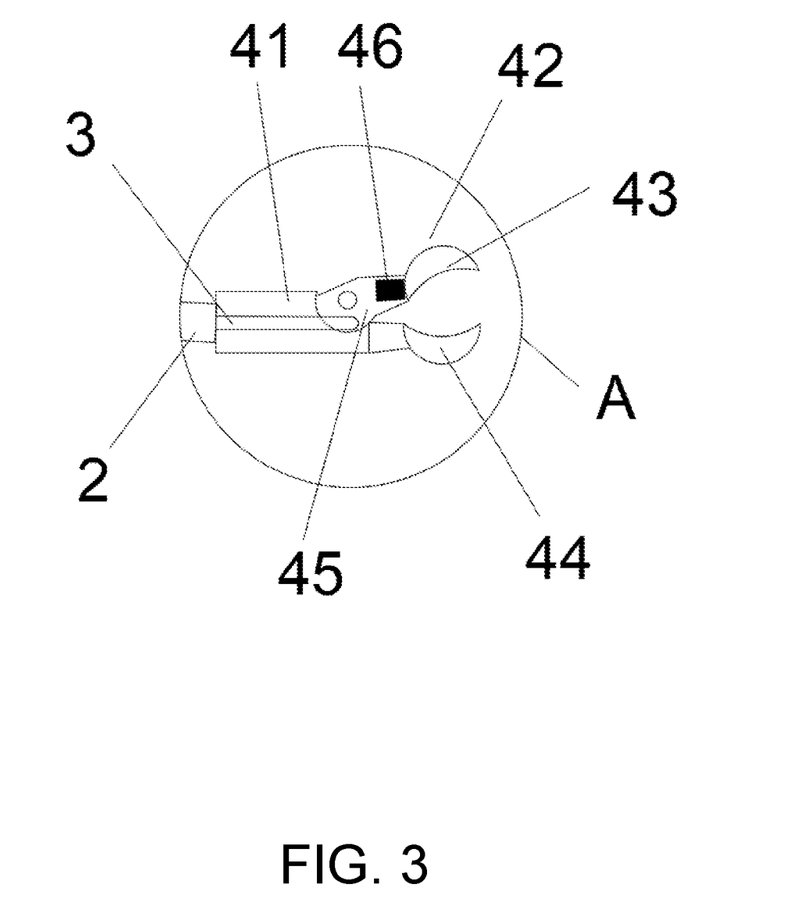
FIG. 3 is an enlarged schematic of A-zone of the embodiments of the disclosure.

As shown in FIG. 1 to FIG. 3, a gold marker recovery device for radiotherapy positioning comprises a positioning gold marker body (5) and a recovery clamp (6) the positioning gold marker (5) comprises a gold marker body (51) and an elastic fixed structure, the elastic fixed structure comprises a fixed segment (52), an extension segment (53) and a spiral segment (54) connected in sequential manner, the fixed segment (52) is embedded in the gold marker body (51), so that the connection between the fixed segment (52) and the gold marker body (51) is tight and the relative sliding or displacement between the fixed segment (52) and the gold marker body (51) is avoided, an end of the gold marker body (51) away from the extension segment (53) is provided with a magnetic ball (55), the recovery clamp (6) comprises an operating handle (1), a rear part of the operating handle (1) is connected with an outer sheath tube (2) in a hollow structure, a zipper (3) for driving the clamp (4) to open and close is movably linked in the outer sheath tube (2).

Further, the fixed segment (52) is embedded in the magnetic ball (55) so that tight connection between the fixed segment (52) and the magnetic ball (55) is guaranteed and relative sliding or displacement between the fixed segment (52) and the magnetic ball (55) can be prevented.

Further, the gold marker body (51) is made of a material that does not project an X-ray.

Further, the elastic fixation structure is made of a superelastic material, such as a memory alloy, which can be but is not limited to nickel-titanium alloy.

Further, when a force is applied to a terminal end of the spiral segment (54) of the elastic fixed structure, the elastic fixed structure becomes straightened or compressed, and when the force disappears, the elastic fixed structure restores to its original shape.

Further, the clamp (4) comprises a support cylinder (41), a distal end of the support cylinder (41) is connected with a clamp head (42), the zipper (3) penetrates a proximal end of the support cylinder (41) and is connected with the clamp head (42), and the clamp head (42) can open and close by pushing and pulling the zipper (3).

Further, the clamp head (42) comprises a first half claw (43) and a second half claw (44), the first half claw (43) is hinged to the support cylinder (41) and the zipper (3) respectively, the second half claw (44) is fixed to the support cylinder (41).

Further, the first half-claw (43) is respectively hinged to the supporting cylinder (41) and the zipper (3) through a connecting part (45), and the connecting part (45) is provided with a permanent magnet (46).

Further, the first half claw (43) and the second half claw (44) are hemispherical.

After the gold marker (5) is implanted into the lesion, the spiral segment (54) is restored to its original shape and is fixed in the trachea of the lesion, and the gold markers (5) are implanted into the lesion by several times. After the treatment, the recovery clamp (6) passes through the channel formed by the medical catheter in the electromagnetic navigation bronchoscope and reaches the position where the positioning gold marker is located, thus retrieving the gold marker; the specific operation process of grasping the positioning gold marker (5) is as follows:

The clamp head (42) approaches the positioning gold marker (5) in open state, and the permanent magnet (46) attracts the magnetic ball (55) to enter the first half claw (43), which can greatly reduce the difficulty of grasping. By pulling the zipper (3), the first half claw (43) and the second half claw (44) come close to each other, so as to improve the stability of grasping. The accuracy of grasping can be further improved because of the magnetic ball (55) on the fixed segment (52) of the positioning gold marker (5).

Embodiment II

As shown in FIG. 1 to FIG. 3, a gold label recovery device for radiotherapy positioning comprises a positioning gold marker (5) and a recovery clamp (6), the positioning gold marker (5) comprises a gold marker body (51) and an elastic fixed structure, the elastic fixed structure comprises a fixed segment (52), an extension segment (53) and a spiral segment (54) connected in a sequential manner, the fixed segment (52) is embedded in the gold marker body (51), so that the connection between the fixed segment (52) and the gold marker body (51) is tight and the relative sliding or displacement between the fixed segment (52) and the gold marker body (51) is avoided, an end of the gold marker body (51) away from the extension segment (53) is provided with a magnetic ball (55), the recovery clamp (6) comprises an operating handle (1), a rear part of the operating handle (1) is connected with an outer sheath tube (2) in a hollow structure, a zipper (3) for driving the clamp (4) to open and close is movably linked in the outer sheath tube (2).

Further, the fixed segment (52) is embedded in the magnetic ball (55) so that tight connection between the fixed segment (52) and the magnetic ball (55) is guaranteed and relative sliding or displacement between the fixed segment (52) and the magnetic ball (55) can be prevented. The contact end of magnetic ball (55) contacted with the gold marker body (51) is flat, which can increase the contact area and avoid sliding, the other end of magnetic ball (55) is spherical; the magnetic ball (55) has a diameter greater than the diameter of the gold marker body (51), which makes the grasp of the recovery clamp (6) at a later stage be more stable.

Further, the gold marker body (51) is made of a material that does not project an X-ray.

Further, the elastic fixation structure is made of a superelastic material, such as a memory alloy, which can be but is not limited to nickel-titanium alloy.

The fixed segment (52) penetrates the gold marker body (51) and the magnetic ball body (55). The connection stability between the fixed segment (52), the gold marker body (51) and the magnetic ball body (55) can be increased by compressing the gold marker body (51) and the magnetic ball body (55), and the relative sliding or displacement between the fixed segment (52), the gold marker body (51) and the magnetic ball body (55) can be avoided. Another method to realize stable connection is to fold the fixed segment (52) reversely into the through hole of the magnetic ball (55) after passing through the magnetic ball (55).

Figure 4:
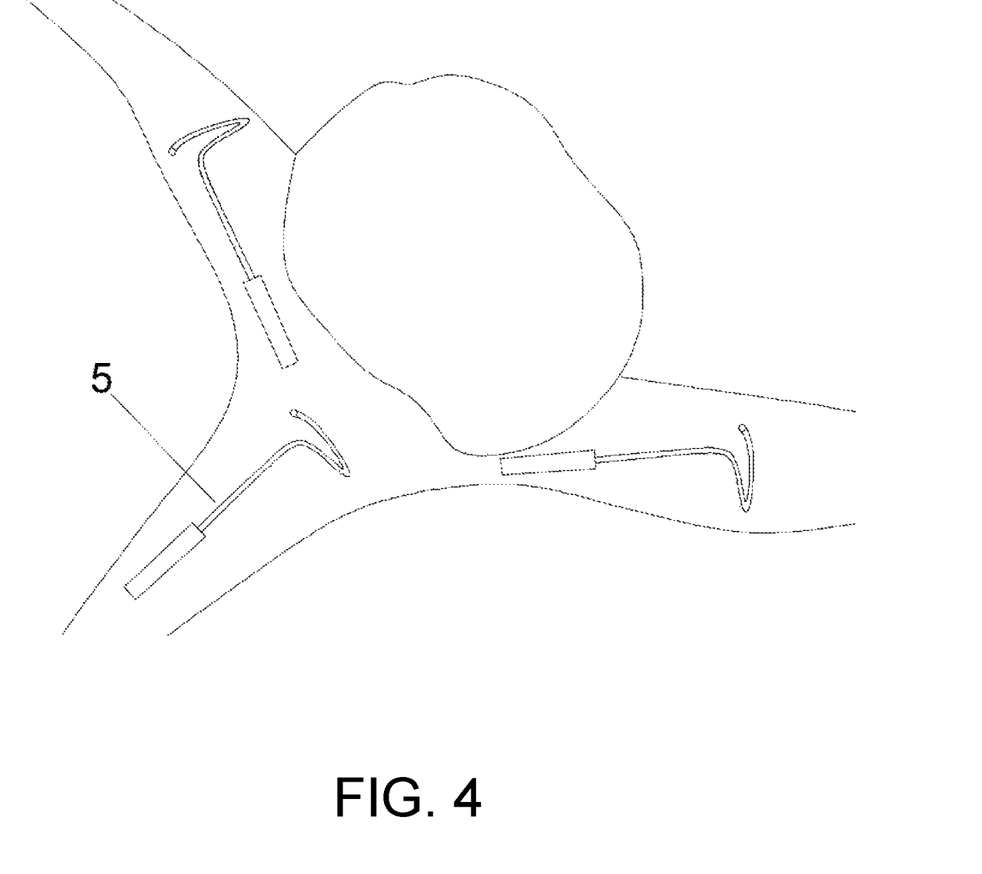
FIG. 4 is a state diagram of the gold marker of the embodiments of the disclosure in use.

As shown in FIG. 4, three positioning gold markers (5) are implanted in the periphery of the central lesion, and the positioning gold marker (5) is implanted through the medical catheter. When the positioning gold marker body (51) is being implanted, the positioning gold marker body (51) is positioned behind the spiral segment (54), and the spiral segment (54) entered the lesion first. Because of the restriction of the wall of the medical catheter, the spiral segment (54) is nearly stretched into a straight line. After being implanted into the lesion area, the spiral segment (54) is restored to its original shape and fixed in the trachea of the lesion. The gold marker (51) is positioned behind the spiral segment (54), so that the gold marker (51) can be retrieved by the recovery clamp (6) at the later stage; after entering the target area, the position of the recovery clamp (6) is corresponding to the position of the gold marker body (51), and the permanent magnet (46) is positioned closest to the magnetic ball (55), which facilitates the grasp.

A using method of the gold label recovery device for radiotherapy positioning comprises the following steps:

S1: Construct a 3D model of the patient's lung according to the three-dimensional reconstruction of two-dimensional CT images to determine the focus area.

S2: Determine several implantation points of the positioning gold marker (5) around the three-dimensional space outside the focus area, the number of the implantation points is 3-6, and the minimum distance between two implantation points shall not be less than 20 mm, a minimum angle of a triangle formed by any three implantation points in the three-dimensional space shall be larger than 15°, a distance from the implantation points to the focus area shall not be greater than 20-30 mm, all the implantation points are visible in a 45° oblique view without overlap;

S3: Plan an implantation path according to the 3D model of the patient's lungs and the several implantation points established.

S4: An electromagnetic navigation bronchoscope reaches the implantation point according to the implantation path established, a medical channel is formed by the electromagnetic navigation bronchoscope after reaching the implantation point, and a positioning gold marker (5) is implanted into the implantation point along the medical channel by a pushing device, and when the positioning gold marker (5) is being implanted, the gold marker body (51) is positioned behind the spiral segment (54), the rest positioning gold markers (5) are implanted into the corresponding implantation points successively in the above way.

S5: After the treatment, plan a removing path according to the latest location information of the positioning gold marker (5) acquired by CT and the 3D model of the patient's lung.

S6: The electromagnetic navigation bronchoscope reaches the target area according to the removing path established, a medical channel is formed by the electromagnetic navigation bronchoscope after reaching the target area, the clamp head (42) of the recovery clamp (6) penetrates through the medical channel in open state and reaches the target area where the positioning gold marker (5) is located, and then the positioning gold marker (5) is retrieved through magnetic attraction force of the permanent magnet (46) and the action of the clamp head (42), and the rest gold markers (5) are removed from the body successively in the above manner.

By utilizing the passage of the human bronchi to realize positioning, the implantation method and the removal method of the disclosure eliminates the risk of the occurrence of pneumothorax and realizes the retrieval of the recyclable gold marker. By precise control of the implantation point in the three-dimensional space around the focus area, the therapeutic dose of the follow-up radiotherapy can be accurately controlled, the therapeutic dose of the treatment area can be increased and the therapeutic dose received by the normal tissue around the irradiation area can be decreased, thus protecting the important organs around the tumor. The spacing between implantation points can be quickly calculated by the coordinate points on the constructed 3D model of the patient's lung, and the minimum angle of the triangle formed by any three reference points in the three-dimensional space can be quickly confirmed to be greater than 15° through the relationship between the spatial coordinate points.

When the lesion in the periphery of the lung is small and the density is low, the range of respiratory movement is large, and gold marker must be implanted for the radiotherapy treatment, so as to carry out the advanced gold marker tracking technology of the cyber knife and truly achieve the tracing and treatment of the target area. The implantation method of the disclosure can effectively avoid the damage to the lung tissue caused during the puncture process and the complications caused by leaving gold marker in the trachea, thus greatly improving the positioning accuracy before the radiotherapy and increasing the success rate of the positioning.

The above description is only the preferred embodiments of the present disclosure and does not constitute a limitation to the protection scope of the present disclosure. For those skilled in the art, the present disclosure may have different variations. Any modification, substitution, improvement, etc. within the spirit and principle of the present disclosure shall fall in the scope of protection of the present disclosure.

What is claimed is:

1. A gold marker recovery device for radiotherapy positioning, comprising a positioning gold marker and a recovery clamp, wherein the positioning gold marker comprises a gold marker body and an elastic fixed structure, the elastic fixed structure comprises a fixed segment, an extending segment and a spiral segment connected in sequential manner, the fixed segment is embedded in the gold marker body so as to realize a tight connection between the fixed segment and the gold marker body and prevent relative sliding or displacement between the fixed segment and the gold marker body, a magnetic ball is arranged at an end of the gold marker body away from the extending segment, and the recovery clamp comprises an operating handle, and an outer sheath tube in a hollow structure is connected to a rear part of the operating handle, a zipper for driving the clamp to open and close is movably connected in the outer sheath tube.

2. A gold marker recovery device for radiotherapy positioning according to claim 1, wherein the fixed segment is embedded in the magnetic ball so as to realize a tight connection between the fixed segment and the magnetic ball and prevent relative sliding or displacement between the fixed segment and the magnetic ball.

3. A gold marker recovery device for radiotherapy positioning according to claim 1, wherein the gold marker body is made of a material that does not project X-rays.

4. A gold marker recovery device for radiotherapy positioning according to claim 1, wherein the elastic fixed structure is made of a super-elastic material.

5. A gold marker recovery device for radiotherapy positioning according to claim 4, wherein when a force is applied to a terminal end of the spiral segment of the elastic fixed structure, the elastic fixed structure becomes straightened or compressed, and when the force disappears the elastic fixed structure restores to original shape.

6. A gold marker recovery device for radiotherapy positioning according to claim 1, wherein the clamp comprises a support cylinder, a distal end of the support cylinder is connected with a clamp head, the zipper penetrates a proximal end of the support cylinder and is connected to the clamp head, and the clamp head is driven to open and close by pushing and pulling the zipper.

7. A gold marker recovery device for radiotherapy positioning according to claim 6, wherein the clamp head comprises a first half claw and a second half claw, the first half claw is respectively hinged to the supporting cylinder and the zipper, and the second half claw is fixed to the support cylinder.

8. A gold marker recovery device for radiotherapy positioning according to claim 7, wherein the first half claw is respectively hinged to the supporting cylinder and the zipper through a connecting part, and the connecting part is provided with a permanent magnet.

9. A gold marker recovery device for radiotherapy positioning according to claim 7, wherein the first half claw and the second half claw are hemispherical.

10. A using method of the gold marker recovery device for radiotherapy positioning according to claim 1 comprising following steps:
   S1: Constructing a 3D model of a patient's lung through a three-dimensional reconstruction of two-dimensional CT images to determine a focus area;
   S2: Determining several implantation points of the positioning gold marker around a three-dimensional space outside the focus area, wherein a number of the implantation points is 3-6, and a minimum distance between two of the implantation points is not less than 20 mm, a minimum angle of a triangle formed by any three of the implantation points in the three-dimensional space is larger than 15°, a distance from one of the implantation points to the focus area is not greater than 20-30 mm, all of the implantation points are visible in a 45° oblique view without overlap;
   S3: Planning an implantation path according to the 3D model of the patient's lungs and the several implantation points established;
   S4: Wherein an electromagnetic navigation bronchoscope reaches the implantation points according to the implantation path established, a medical channel is formed by the electromagnetic navigation bronchoscope after reaching the implantation points, and the positioning gold marker is implanted into the implantation points along the medical channel by a pushing device, and when the positioning gold marker is implanted, the gold marker body is positioned behind the spiral segment, other positioning gold markers are implanted into corresponding implantation points successively in the above way;
   S5: After the treatment, planning a removal path according to a latest location information of the positioning gold marker acquired by CT and the 3D model of the patient's lung; and
   S6: Wherein electromagnetic navigation bronchoscope reaches a target area according to a removing path established, a medical channel is formed by the electromagnetic navigation bronchoscope after reaching the target area, a clamp head of the recovery clamp penetrates through the medical channel in open state and reaches the target area where the positioning gold marker is located, and then the positioning gold marker is retrieved through magnetic attraction force of a permanent magnet and an action of the clamp head, and the other gold markers are removed successively in the above manner.

11. A using method of the gold marker recovery device for radiotherapy positioning according to claim 2 comprising following steps:
   S1: Constructing a 3D model of a patient's lung through a three-dimensional reconstruction of two-dimensional CT images to determine a focus area;
   S2: Determining several implantation points of the positioning gold marker around a three-dimensional space outside the focus area, wherein a number of the implantation points is 3-6, and a minimum distance between two of the implantation points is not less than 20 mm, a minimum angle of a triangle formed by any three of the implantation points in the three-dimensional space is larger than 15°, a distance from one of the implantation points to the focus area is not greater than 20-30 mm, all of the implantation points are visible in a 45° oblique view without overlap;
   S3: Planning an implantation path according to the 3D model of the patient's lungs and the several implantation points established;
   S4: Wherein an electromagnetic navigation bronchoscope reaches the implantation points according to the implantation path established, a medical channel is formed by the electromagnetic navigation bronchoscope after reaching the implantation points, and the positioning gold marker is implanted into the implantation points along the medical channel by a pushing device, and when the positioning gold marker is implanted, the gold marker body is positioned behind the spiral segment, other positioning gold markers are implanted into corresponding implantation points successively in the above way;
   S5: After the treatment, planning a removal path according to a latest location information of the positioning gold marker acquired by CT and the 3D model of the patient's lung; and
   S6: Wherein electromagnetic navigation bronchoscope reaches a target area according to a removing path established, a medical channel is formed by the electromagnetic navigation bronchoscope after reaching the target area, a clamp head of the recovery clamp penetrates through the medical channel in open state and reaches the target area where the positioning gold marker is located, and then the positioning gold marker is retrieved through magnetic attraction force of a permanent magnet and an action of the clamp head, and the other gold markers are removed successively in the above manner.

12. A using method of the gold marker recovery device for radiotherapy positioning according to claim 3 comprising following steps:
   S1: Constructing a 3D model of a patient's lung through a three-dimensional reconstruction of two-dimensional CT images to determine a focus area;

S2: Determining several implantation points of the positioning gold marker around a three-dimensional space outside the focus area, wherein a number of the implantation points is 3-6, and a minimum distance between two of the implantation points is not less than 20 mm, a minimum angle of a triangle formed by any three of the implantation points in the three-dimensional space is larger than 15°, a distance from one of the implantation points to the focus area is not greater than 20-30 mm, all of the implantation points are visible in a 45° oblique view without overlap;

S3: Planning an implantation path according to the 3D model of the patient's lungs and the several implantation points established;

S4: Wherein an electromagnetic navigation bronchoscope reaches the implantation points according to the implantation path established, a medical channel is formed by the electromagnetic navigation bronchoscope after reaching the implantation points, and the positioning gold marker is implanted into the implantation points along the medical channel by a pushing device, and when the positioning gold marker is implanted, the gold marker body is positioned behind the spiral segment, other positioning gold markers are implanted into corresponding implantation points successively in the above way;

S5: After the treatment, planning a removal path according to a latest location information of the positioning gold marker acquired by CT and the 3D model of the patient's lung; and S6: Wherein electromagnetic navigation bronchoscope reaches a target area according to a removing path established, a medical channel is formed by the electromagnetic navigation bronchoscope after reaching the target area, a clamp head of the recovery clamp penetrates through the medical channel in open state and reaches the target area where the positioning gold marker is located, and then the positioning gold marker is retrieved through magnetic attraction force of a permanent magnet and an action of the clamp head, and the other gold markers are removed successively in the above manner.

13. A using method of the gold marker recovery device for radiotherapy positioning according to claim 4 comprising following steps:

S1: Constructing a 3D model of a patient's lung through a three-dimensional reconstruction of two-dimensional CT images to determine a focus area;

S2: Determining several implantation points of the positioning gold marker around a three-dimensional space outside the focus area, wherein a number of the implantation points is 3-6, and a minimum distance between two of the implantation points is not less than 20 mm, a minimum angle of a triangle formed by any three of the implantation points in the three-dimensional space is larger than 15°, a distance from one of the implantation points to the focus area is not greater than 20-30 mm, all of the implantation points are visible in a 45° oblique view without overlap;

S3: Planning an implantation path according to the 3D model of the patient's lungs and the several implantation points established;

S4: Wherein an electromagnetic navigation bronchoscope reaches the implantation points according to the implantation path established, a medical channel is formed by the electromagnetic navigation bronchoscope after reaching the implantation points, and the positioning gold marker is implanted into the implantation points along the medical channel by a pushing device, and when the positioning gold marker is implanted, the gold marker body is positioned behind the spiral segment, other positioning gold markers are implanted into corresponding implantation points successively in the above way;

S5: After the treatment, planning a removal path according to a latest location information of the positioning gold marker acquired by CT and the 3D model of the patient's lung; and S6: Wherein electromagnetic navigation bronchoscope reaches a target area according to a removing path established, a medical channel is formed by the electromagnetic navigation bronchoscope after reaching the target area, a clamp head of the recovery clamp penetrates through the medical channel in open state and reaches the target area where the positioning gold marker is located, and then the positioning gold marker is retrieved through magnetic attraction force of a permanent magnet and an action of the clamp head, and the other gold markers are removed successively in the above manner.

14. A using method of the gold marker recovery device for radiotherapy positioning according to claim 5 comprising following steps:

S1: Constructing a 3D model of a patient's lung through a three-dimensional reconstruction of two-dimensional CT images to determine a focus area;

S2: Determining several implantation points of the positioning gold marker around a three-dimensional space outside the focus area, wherein a number of the implantation points is 3-6, and a minimum distance between two of the implantation points is not less than 20 mm, a minimum angle of a triangle formed by any three of the implantation points in the three-dimensional space is larger than 15°, a distance from one of the implantation points to the focus area is not greater than 20-30 mm, all of the implantation points are visible in a 45° oblique view without overlap;

S3: Planning an implantation path according to the 3D model of the patient's lungs and the several implantation points established;

S4: Wherein an electromagnetic navigation bronchoscope reaches the implantation points according to the implantation path established, a medical channel is formed by the electromagnetic navigation bronchoscope after reaching the implantation points, and the positioning gold marker is implanted into the implantation points along the medical channel by a pushing device, and when the positioning gold marker is implanted, the gold marker body is positioned behind the spiral segment, other positioning gold markers are implanted into corresponding implantation points successively in the above way;

S5: After the treatment, planning a removal path according to a latest location information of the positioning gold marker acquired by CT and the 3D model of the patient's lung; and S6: Wherein electromagnetic navigation bronchoscope reaches a target area according to a removing path established, a medical channel is formed by the electromagnetic navigation bronchoscope after reaching the target area, a clamp head of the recovery clamp penetrates through the medical channel in open state and reaches the target area where the positioning gold marker is located, and then the positioning gold marker is retrieved through magnetic attraction force of a permanent magnet and an action of the clamp head, and the other gold markers are removed successively in the above manner.

15. A using method of the gold marker recovery device for radiotherapy positioning according to claim 6 comprising following steps:
   S1: Constructing a 3D model of a patient's lung through a three-dimensional reconstruction of two-dimensional CT images to determine a focus area;
   S2: Determining several implantation points of the positioning gold marker around a three-dimensional space outside the focus area, wherein a number of the implantation points is 3-6, and a minimum distance between two of the implantation points is not less than 20 mm, a minimum angle of a triangle formed by any three of the implantation points in the three-dimensional space is larger than 15°, a distance from one of the implantation points to the focus area is not greater than 20-30 mm, all of the implantation points are visible in a 45° oblique view without overlap;
   S3: Planning an implantation path according to the 3D model of the patient's lungs and the several implantation points established;
   S4: Wherein an electromagnetic navigation bronchoscope reaches the implantation points according to the implantation path established, a medical channel is formed by the electromagnetic navigation bronchoscope after reaching the implantation points, and the positioning gold marker is implanted into the implantation points along the medical channel by a pushing device, and when the positioning gold marker is implanted, the gold marker body is positioned behind the spiral segment, other positioning gold markers are implanted into corresponding implantation points successively in the above way;
   S5: After the treatment, planning a removal path according to a latest location information of the positioning gold marker acquired by CT and the 3D model of the patient's lung; and
   S6: Wherein electromagnetic navigation bronchoscope reaches a target area according to a removing path established, a medical channel is formed by the electromagnetic navigation bronchoscope after reaching the target area, the clamp head of the recovery clamp penetrates through the medical channel in open state and reaches the target area where the positioning gold marker is located, and then the positioning gold marker is retrieved through magnetic attraction force of a permanent magnet and an action of the clamp head, and the other gold markers are removed successively in the above manner.

16. A using method of the gold marker recovery device for radiotherapy positioning according to claim 7 comprising following steps:
   S1: Constructing a 3D model of a patient's lung through a three-dimensional reconstruction of two-dimensional CT images to determine a focus area;
   S2: Determining several implantation points of the positioning gold marker around a three-dimensional space outside the focus area, wherein a number of the implantation points is 3-6, and a minimum distance between two of the implantation points is not less than 20 mm, a minimum angle of a triangle formed by any three of the implantation points in the three-dimensional space is larger than 15°, a distance from one of the implantation points to the focus area is not greater than 20-30 mm, all of the implantation points are visible in a 45° oblique view without overlap;
   S3: Planning an implantation path according to the 3D model of the patient's lungs and the several implantation points established;
   S4: Wherein an electromagnetic navigation bronchoscope reaches the implantation points according to the implantation path established, a medical channel is formed by the electromagnetic navigation bronchoscope after reaching the implantation points, and the positioning gold marker is implanted into the implantation points along the medical channel by a pushing device, and when the positioning gold marker is implanted, the gold marker body is positioned behind the spiral segment, other positioning gold markers are implanted into corresponding implantation points successively in the above way;
   S5: After the treatment, planning a removal path according to a latest location information of the positioning gold marker acquired by CT and the 3D model of the patient's lung; and
   S6: Wherein electromagnetic navigation bronchoscope reaches a target area according to a removing path established, a medical channel is formed by the electromagnetic navigation bronchoscope after reaching the target area, a clamp head of the recovery clamp penetrates through the medical channel in open state and reaches the target area where the positioning gold marker is located, and then the positioning gold marker is retrieved through magnetic attraction force of a permanent magnet and an action of the clamp head, and the other gold markers are removed successively in the above manner.

17. A using method of the gold marker recovery device for radiotherapy positioning according to claim 8 comprising following steps:
   S1: Constructing a 3D model of a patient's lung through a three-dimensional reconstruction of two-dimensional CT images to determine a focus area;
   S2: Determining several implantation points of the positioning gold marker around a three-dimensional space outside the focus area, wherein a number of the implantation points is 3-6, and a minimum distance between two of the implantation points is not less than 20 mm, a minimum angle of a triangle formed by any three of the implantation points in the three-dimensional space is larger than 15°, a distance from one of the implantation points to the focus area is not greater than 20-30 mm, all of the implantation points are visible in a 45° oblique view without overlap;
   S3: Planning an implantation path according to the 3D model of the patient's lungs and the several implantation points established;
   S4: Wherein an electromagnetic navigation bronchoscope reaches the implantation points according to the implantation path established, a medical channel is formed by the electromagnetic navigation bronchoscope after reaching the implantation points, and the positioning gold marker is implanted into the implantation points along the medical channel by a pushing device, and when the positioning gold marker is implanted, the gold marker body is positioned behind the spiral segment, other positioning gold markers are implanted into corresponding implantation points successively in the above way;

S5: After the treatment, planning a removal path according to a latest location information of the positioning gold marker acquired by CT and the 3D model of the patient's lung; and S6: Wherein electromagnetic navigation bronchoscope reaches a target area according to a removing path established, a medical channel is formed by the electromagnetic navigation bronchoscope after reaching the target area, a clamp head of the recovery clamp penetrates through the medical channel in open state and reaches the target area where the positioning gold marker is located, and then the positioning gold marker is retrieved through magnetic attraction force of the permanent magnet and an action of the clamp head, and the other gold markers are removed successively in the above manner.

18. A using method of the gold marker recovery device for radiotherapy positioning according to claim 9 comprising following steps:

S1: Constructing a 3D model of a patient's lung through a three-dimensional reconstruction of two-dimensional CT images to determine a focus area;

S2: Determining several implantation points of the positioning gold marker around a three-dimensional space outside the focus area, wherein a number of the implantation points is 3-6, and a minimum distance between two of the implantation points is not less than 20 mm, a minimum angle of a triangle formed by any three of the implantation points in the three-dimensional space is larger than 15°, a distance from one of the implantation points to the focus area is not greater than 20-30 mm, all of the implantation points are visible in a 45° oblique view without overlap;

S3: Planning an implantation path according to the 3D model of the patient's lungs and the several implantation points established;

S4: Wherein an electromagnetic navigation bronchoscope reaches the implantation points according to the implantation path established, a medical channel is formed by the electromagnetic navigation bronchoscope after reaching the implantation points, and the positioning gold marker is implanted into the implantation points along the medical channel by a pushing device, and when the positioning gold marker is implanted, the gold marker body is positioned behind the spiral segment, other positioning gold markers are implanted into corresponding implantation points successively in the above way;

S5: After the treatment, planning a removal path according to a latest location information of the positioning gold marker acquired by CT and the 3D model of the patient's lung; and S6: Wherein electromagnetic navigation bronchoscope reaches a target area according to a removing path established, a medical channel is formed by the electromagnetic navigation bronchoscope after reaching the target area, a clamp head of the recovery clamp penetrates through the medical channel in open state and reaches the target area where the positioning gold marker is located, and then the positioning gold marker is retrieved through magnetic attraction force of a permanent magnet and an action of the clamp head, and the other gold markers are removed successively in the above manner.

* * * * *